United States Patent
Rathjen

(10) Patent No.: US 7,264,355 B2
(45) Date of Patent: Sep. 4, 2007

(54) OPHTHALMOLOGIC DEVICE AND OPHTHALMOLOGIC MEASURING METHOD

(75) Inventor: Christian Rathjen, Bremen (DE)

(73) Assignee: SIS AG Surgical Instrument Systems, Brugg b. Biel (CH)

(*) Notice: Subject to any disclaimer, the term of this patent is extended or adjusted under 35 U.S.C. 154(b) by 729 days.

(21) Appl. No.: 10/730,923

(22) Filed: Dec. 10, 2003

(65) Prior Publication Data

US 2004/0119943 A1    Jun. 24, 2004

(30) Foreign Application Priority Data

Dec. 16, 2002  (EP) ................... 02406102

(51) Int. Cl.
*A61B 3/00*    (2006.01)
*A61B 3/14*    (2006.01)

(52) U.S. Cl. ..................... 351/221; 351/206
(58) Field of Classification Search ......... 351/200–223
See application file for complete search history.

(56) References Cited

U.S. PATENT DOCUMENTS 4,523,821 A * 6/1985 Lang et al. ............ 351/214
5,202,708 A   4/1993 Sasaki et al. ............ 351/206
5,341,180 A * 8/1994 Isogai et al. ............ 351/206

FOREIGN PATENT DOCUMENTS

EP    0 933 060 A1    8/1999

* cited by examiner

Primary Examiner—Hung Dang
Assistant Examiner—Mohammed Hasan
(74) Attorney, Agent, or Firm—Oliff & Berridge, PLC

(57) ABSTRACT

Proposed are an ophthalmologic device and an ophthalmologic measuring method in which, by means of a light projector, a beam of rays, for example a light slit, is projected through a cross-sectional portion of an eye, in particular through a cross-sectional portion of the cornea of the eye. A cross-sectional image of at least one sub-area of the cross-sectional portion illuminated by the light projector is captured by image-capturing means which are disposed in Scheimpflug configuration with respect to the beam of rays. A view image of the eye, comprising an image of the cross-sectional portion illuminated by the first light projector, is captured by further image-capturing means and is stored assigned to the captured cross-sectional image. The relative position of the stored cross-sectional image to the eye is determined on the basis of the stored assigned view image, and the stored cross-sectional image is positioned relative to previously stored cross-sectional images of the eye. A coherent examination of the entire eye is made possible in which the relative movements of the eye with respect to the device are taken into consideration.

28 Claims, 5 Drawing Sheets

OPHTHALMOLOGIC DEVICE AND OPHTHALMOLOGIC MEASURING METHOD

TECHNICAL FIELD

The present invention relates to an ophthalmologic device and an ophthalmologic measuring method. The invention relates in particular to an ophthalmologic device and an ophthalmologic measuring method in which, by means of a light projector, a beam of rays is projected through a cross-sectional portion of an eye, in particular through a cross-sectional portion of the cornea, in which by means of first image-capturing means, which are disposed in Scheimpflug configuration with respect to the beam of rays, a cross-sectional image of at least a sub-area of the cross-sectional portion, illuminated by the light projector, is captured from a first position outside the beam of rays and is stored, and in which by means of second image-capturing means a view image of the eye is captured and is stored assigned to the captured cross-sectional image.

BACKGROUND ART

Known in the state of the art are ophthalmologic devices and ophthalmologic measuring methods in which, by means of a light projector, a beam of rays is projected through a cross-sectional portion of an eye, in particular through a cross-sectional portion of the cornea. Typically, the beam of rays is projected in the form of a light slit. Described in the patent publication U.S. Pat. No. 5,404,884 is a method and a device for examining corneal tissue of a patient. According to U.S. Pat. No. 5,404,884, a substantially planer laser beam with a slit-like profile is directed through a cross-sectional portion of the cornea. By capturing at least a portion of the light scattered in the cornea, i.e. at least a portion of the light slit, a cross-sectional image of the cornea is obtained, according to U.S. Pat. No. 5,404,884. From a multiplicity of such cross-sectional images of the cornea, corneal haze, corneal thickness and corneal topography can be determined comprehensively for the whole cornea, according to U.S. Pat. No. 5,404,884. Since the eyes can move relative to the examination device, examination of the entire eye as set forth in U.S. Pat. No. 5,404,884 can lead to inaccuracies, however, because these relative movements are not registered and taken into account. In the professional article B. R. Masters et al., "Transformation of a Set of Slices Rotated on a Common Axis to a Set of Z-Slices: Application to Three-Dimensional Visualization of the In Vivo Human Lens," *Computerized Medical Imaging and Graphics*, Vol. 21, No. 3, pages 145 to 151, 1997, it is explicitly pointed out moreover that with comprehensive examination of the eye based on the merging of a multiplicity of cross-sectional images, measurement artifacts can result as a consequence of the difficulty of mutual alignment of the individual cross-sectional images.

Described in the patent publication U.S. Pat. No. 4,711,541 is an ophthalmologic device having a slit lamp for projection of a light slit on the lens of an eye. The device according to U.S. Pat. No. 4,711,541 comprises in addition a photo camera disposed according to Scheimpflug conditions with respect to the plane of the light slit in order to image sharply the entire cross-sectional portion of the crystalline lens which is illuminated by the light slit. The device according to U.S. Pat. No. 4,711,541 has a stereo microscope in order to enable the user to have a top view of the eye. By means of optical elements of the device, the top view can be supplied to the camera for depiction. However, by means of polarizing filters, it is thereby ensured that not the light slit reflected on the surface of the crystalline lens but instead only the background illumination of the eye, visible in the top view, coming from the reflection of the light slit on the ocular fundus and the scattering by the crystalline lens, is supplied to the photo camera for imaging. By means of a movable mirror, the light section in the crystalline lens and the top view of the eye with the background illumination can be pictured next to each other on the same photograph. Since the device according to U.S. Pat. No. 4,711,541 only allows an examination with individual pictures, no coherent examination of the whole eye can be carried out.

Described in the patent publication U.S. Pat. No. 5,341,180 is an ophthalmologic photographing apparatus which projects a light slit on the eye by means of a slit lamp. The photographing apparatus comprises a CCD camera (Charged Couple Device) which is disposed with respect to the plane of the light slit according to Scheimpflug conditions, in order to image sharply the entire cross-sectional portion of the eye illuminated by the light slit. The apparatus according to U.S. Pat. No. 5,341,180 comprises a second CCD camera providing the user with a top view of the eye to be examined and serving to align the apparatus, or respectively the eye, with the aid of light markers projected on the eye. The apparatus according to U.S. Pat. No. 5,341,180 has polarizing filters in order to prevent the light slit from being visible in the top view of the second CCD camera. In order to facilitate precise alignments, the patient to be examined has to focus his eyes on fixing markers with the taking of each picture, which the patient can find tedious during an examination of the entire eye and which is also time-consuming.

DISCLOSURE OF INVENTION

It is an object of the present invention to propose a new ophthalmologic device and a new ophthalmologic measuring method which do not have the drawbacks of the state of the art, and which in particular make possible a coherent examination of the entire eye, in particular determination of topography and measurement values for structures of the anterior chamber of the eye, for example the corneal topography and corneal thickness, relative movements of the eye with respect to the device being taken into account.

The ophthalmologic device comprises a first light projector for projection of a beam of rays through a cross-sectional portion of an eye, in particular through a cross-sectional portion of the cornea of the eye, first image-capturing means for capturing and storing a cross-sectional image of at least one sub-area of the cross-sectional portion, illuminated by the first light projector, from a first position outside the beam of rays, which means are disposed in Scheimpflug configuration with respect to the beam of rays, and second image-capturing means for capturing a view image of the eye and for storing the captured view image assigned to the captured cross-sectional image.

The above-mentioned objects are achieved through the invention in particular in that the second image-capturing means of this ophthalmologic device are set up to capture and store the view image in such a way that the view image comprises an image of the cross-sectional portion illuminated by the first light projector, and that this ophthalmologic device comprises processing means for positioning the stored cross-sectional image relative to the eye on the basis of the stored assigned view image. The capturing and storing of the cross-sectional image and the view image belonging thereto with the illuminated cross-sectional portion makes possible the determination of the position of the cross-sectional image, respectively the illuminated cross-sectional portion captured therein, relative to the eye on the basis of the assigned view image, which, in turn, makes possible a coherent examination of the whole eye with a multiplicity of cross-sectional images, relative movements of the eye being able to be taken into consideration on the basis of the determined positions of the respective cross-sectional images. Used as points of reference for the position determination can be natural features of the eye such as limbus, iris or pupil, which are pictured in the view image. Since for each cross-sectional image the relative position is also automatically determined, the whole eye can be examined in an interrelated way in that a multiplicity of cross-sectional images are merged, corresponding to their assigned position, into a three-dimensional image of the eye. A coherent examination of the whole eye is made possible during which relative movements of the eye to the device are taken into account, without the patient to be examined having to focus his eyes on fixing markers with the taking of each picture in order to prevent measurement errors. From a multiplicity of cross-sectional images which are merged corresponding to their determined position, corneal thickness, corneal topography and/or corneal haze can be determined, for instance, in a comprehensive way for the whole cornea of the eye. The processing means are preferably designed to position a multiplicity of stored cross-sectional images relative to one another on the basis of the stored view images assigned to them in each case.

In an embodiment variant, the processing means are designed to determine the thickness of the cross-sectional portion, illuminated by the first light projector, of the eye on the basis of the stored view image. Since the beam of rays projected by the first light projector has a finite thickness and can be divergent, the thickness of the illuminated cross-sectional portion in the cross-sectional image captured outside the beam of rays appears larger or smaller depending upon the thickness of the beam of rays. The determination of the thickness of the cross-sectional part of the eye illuminated by the first light projector has the advantage that the influence of the finite thickness of the beam of rays can be taken into consideration during the thickness measurement of illuminated cross-sectional portions of the eye, for instance during corneal thickness measurement, and the thickness measurement can be corrected accordingly, which leads to higher precision of measurement. For determination of the thickness of the cross-sectional portion illuminated by the first light projector, respectively of the beam of rays, an image of a top view has proven to be especially advantageous, i.e. a view image in which the second image-capturing means are disposed such that its optic axis runs substantially parallel to the optic axis or the line of vision of the eye, or coincides with the optic axis or the line of vision of the eye, because it is in particular precise and simple when the optic axis of the second image-capturing means coincides with the beam of rays running through the cross-sectional portion.

The preferred disposition of the second image-capturing means and of the first light projector in which the optic axis of the second image-capturing means coincides with the beam of rays running through the cross-sectional portion also makes possible, in a preferred way, a particularly simple and precise determination of position of the depicted illuminated cross-sectional portion, especially when the eye is captured as view image by the second image-capturing means.

In a preferred embodiment variant, the first and the second image-capturing means are disposed such that their optic axes lie in a common plane. By means of this configuration the cross-sectional images captured by first image-capturing means and the assigned view images captured by second image-capturing means can be more simply related to one another geometrically than is possible with alternative configurations, which simplifies the relative positioning of a multiplicity of cross-sectional images to one another and the merging of these cross-sectional images.

Preferably, the first and the second image-capturing means comprise a common image converter, and the first image-capturing means comprise ray-redirecting optical elements, the ray-redirecting optical elements being disposed such that, for generation of the cross-sectional image, light rays are redirected to the common image converter. In an alternative embodiment variant, the first and second image-capturing means comprise a common image converter, and the second image-capturing means comprise ray-redirecting optical elements, the ray-redirecting optical elements being disposed such that light rays are redirected to the common image converter for generation of the view image. Both of these embodiment variants have the advantage that they have only one image converter, and thus can be designed more economically and more compactly than an alternative embodiment with two separate image converters. The first-mentioned, preferred variant of these two embodiment possibilities has moreover the advantage that the first image-capturing means can be provided in a simple and compact way with further ray-redirecting optical elements, so that light rays can be redirected to the common image converter from different positions for generation of a multiplicity of cross-sectional images.

The first image-capturing means are preferably set up to capture and store a second cross-sectional image of the sub-area of the cross-sectional portion illuminated by the first light projector, from a second position outside the beam of rays simultaneously with the capturing of the first cross-sectional image, the first position and the second position lying on different sides of a plane situated in the beam of rays, and the illuminated cross-sectional portion being captured, for instance, at an observation angle of equal size. The advantage of capturing images of the illuminated cross-sectional portion from a multiplicity of positions is that a multiplicity of measuring results can be determined and from them more precise measuring results obtained through averaging. In averaging, discrepancies in the determination of a first distance between eye structures in the first cross-sectional image and a second distance between eye structures in the second cross-sectional image cancel each other out, for example. If, therefore, the ophthalmologic device is used in such a way that the beam of rays is projected substantially perpendicular to the (corneal) surface, turned toward the light projector, of the eye, slight angular misalignments of the beam of rays with respect to the normal to the surface, turned toward the light projector, of the cornea do not have an effect upon the determination of the corneal thickness, for instance. Even when the device is applied such that the beam of rays is projected substantially along the optic axis of the eye, slight angular misalignments and eccentricities of the beam of rays, i.e. shifts from the vertex of the eye, do not have an effect upon the determination of the corneal thickness. The same applies to small deviations of the observation angle from the first position with respect to the observation angle from the second position. The advantage of capturing two cross-sectional images from different positions at equal observation angles is therefore that small inaccuracies in the application, the adjustment and/or the calibration of the ophthalmologic device do not result in any large deviations in the measuring results. If the ophthalmologic device is applied in meridional sections, for example, then a calibration in meridional section suffices in order to be able to measure precisely even with slight eccentricities and angular misalignments. The ophthalmologic device thus makes possible a simpler application and implementation while maintaining the precision of the measuring results.

In the embodiment variant in which the first image-capturing means comprise an image converter and further ray-redirecting optical elements, preferably first of the ray-redirecting elements are disposed at the first position such that light rays are redirected to the image converter for generation of the first cross-sectional image, and second of the ray-redirecting optical elements are disposed at the second position such that light rays are redirected to the image converter for generation of the second cross-sectional image. This results in an especially compact and economical design.

In an embodiment variant, the ophthalmologic device comprises one or more additional second light projectors for projection of light markers on the eye, and the second image-capturing means are synchronized with the first light projector and with the second light projectors in such a way that, during the capturing and storing of the view image of the eye, the image of the cross-sectional portion illuminated by the first light projector and an image of the light markers projected by the second light projectors are co-captured and co-stored. The projected and co-captured light markers serve as artificial reference marks which can be used for determination of the relative position of the ophthalmologic device to the eye and thus for position determination of the cross-sectional image, or respectively the illuminated cross-sectional portion.

In an embodiment variant, the ophthalmologic device comprises a screen element with a visible pattern, which screen element is disposed such that the visible pattern is situated on a side of the screen element turned toward the eye during application of the device, and such that the beam of rays is able to be projected unimpeded through the cross-sectional portion of the eye, and such that the cross-sectional image and the view image are able to be captured by the first, respectively second, image-capturing means in an unimpeded way. Since the visible pattern, for instance a placido pattern, is reflected by the eye, it can be captured with the view image and can be used as an artificial reference pattern for determination of the relative position of the ophthalmologic device to the eye and thus for position determination of the cross-sectional image, or respectively the illuminated cross-sectional portion.

In an embodiment variant, the ophthalmologic device comprises drive means to rotate the first light projector and the first and the second image-capturing means substantially about a normal to the surface of the eye turned toward the first light projector or to shift them substantially perpendicular to this normal. Made possible by means of these drive means is an automated interrelated examination of the whole eye based on a multiplicity of cross-sectional images.

Preferably, the first light projector is designed such that it projects the beam of rays in the form of a light slit. Although other shapes for the beam of rays can be used, for example punctiform, a beam of rays in the shape of a light slit is especially suitable for the coherent examination of the whole eye based on a multiplicity of light sections of the eye.

Preferably, the second image-capturing means are disposed such that their optic axis coincides with the optic axis of the eye, or runs substantially parallel to the optic axis of the eye. The eye can thereby be captured as an image of a top view, which is advantageous both for the determination of position of the illuminated cross-sectional portion as well as for the determination of thickness of the illuminated cross-sectional portion, as has already been explained in the foregoing. In combination with the preferred disposition of the two image-capturing means and of the first light projector, in which the optic axis of the second image-capturing means coincides with the beam of rays running through the cross-sectional portion, there results a configuration in which the first light projector projects the beam of rays such that the beam of rays coincides with the optic axis of the eye or such that the beam of rays runs parallel to the optic axis of the eye.

BRIEF DESCRIPTION OF DRAWINGS

An embodiment of the present invention will be described in the following with reference to an example. The example of the embodiment is illustrated by the following attached figures.

MODES FOR CARRYING OUT THE INVENTION

Figure 1A:
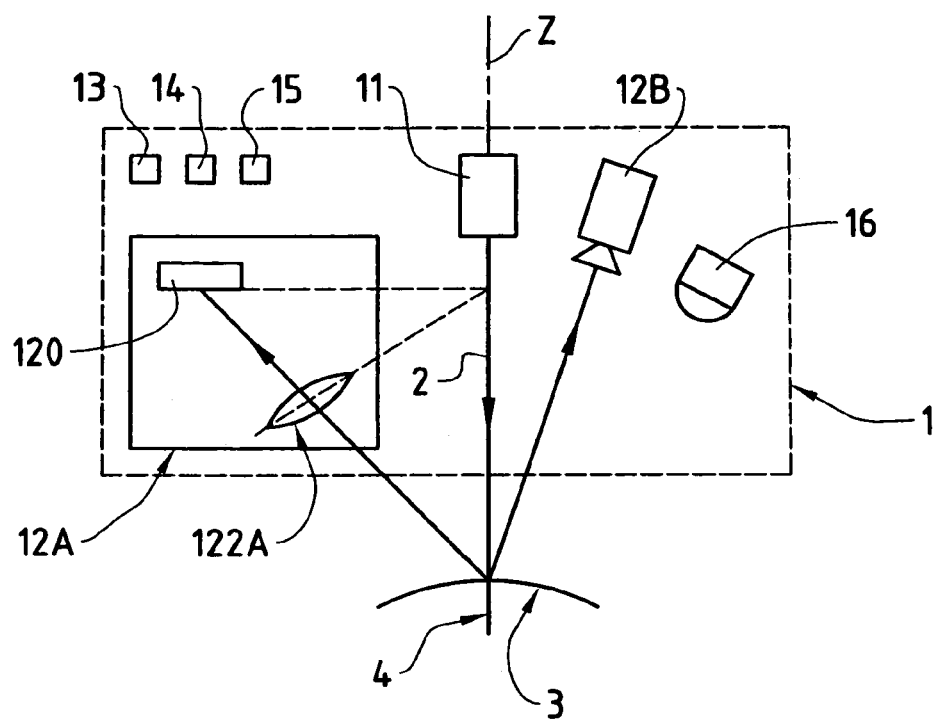
FIG. 1a shows a block diagram illustrating schematically an ophthalmologic device with a light projector, an image-capturing device for capturing a cross-sectional image of an eye, an image-capturing device for capturing a view image of the eye as well as an additional light source.

In the FIGS. 1a, 2a, 4, 5, 6, 7 and 9, the reference numeral 1 designates an ophthalmologic device, different embodiments of the ophthalmologic device 1 being explained in the following description with reference to these figures. Otherwise same, corresponding components are designated in the figures by the same reference numerals.

The embodiments of the ophthalmologic device 1 shown in FIGS. 1a, 2a, 4, 5, 6, 7 and 9 comprise a light projector 11 for projection of a beam of rays 2 through a cross-sectional portion of an eye 3, in particular through a cross-sectional portion of the cornea 30 of the eye 3. The beam of rays 2 is projected preferably in the form of a light slit. The light projector 11 comprises, for example, a slit lamp or a laser whose light is shaped into a fan through beam transformation optics.

The embodiments of the ophthalmologic device 1 shown in FIGS. 1a, 2a, 4, 5, 6, 7 and 9 comprise image-capturing means for capturing and storing a cross-sectional image 30A of at least one sub-area of the cross-sectional portion 4 illuminated by the light projector 11, which means are disposed in Scheimpflug configuration with respect to the beam of rays 2.

The embodiments of the ophthalmologic device 1 shown in FIGS. 1a, 2a, 4, 5, 6, 7 and 9 comprise moreover further image-capturing means for capturing a view image 3A of the eye 3, which comprises an image of the illuminated cross-sectional portion 4A, and for storing the captured view image 3A, and the image of the illuminated cross-sectional portion 4A contained therein, assigned to the captured cross-sectional image 30A.

As shown in FIGS. 1a, 2a, 4, 5, 6, 7 and 9, the image-capturing means comprise, depending upon embodiment of the ophthalmologic device 1, image-capturing devices 12A, 12B, for instance CCD cameras (Charged Coupled Device) or CMOS cameras (Complementary Metal-Oxide-Silicon), image converter 120, for example CCD chips or CMOS chips, ray-redirecting optical elements 121A, 121B, 121E, for instance mirrors, ray-redirecting optical elements 121C, 121D, for example beam-splitting optical elements such as semi-transparent mirrors, and/or imaging optical elements 122A, 122B, 122C, for instance lenses.

To make natural eye features visible, such as limbus 33, iris 34, or pupil 35, and/or to project artificial light markers 36, the embodiments of the ophthalmologic device 1 shown in FIGS. 1a, 2a, 4, 5, 6, 7 and 9 comprise one or more additional light sources 16. In particular to make natural eye features visible, one or more infrared light-emitting diodes can be used, for instance. The natural and/or artificial reference features are co-captured in the view image 3A of the eye 3.

The embodiments of the ophthalmologic device 1 shown in FIGS. 1a, 2a, 4, 5, 6, 7 and 9 comprise processing means 13 with functional modules for processing captured view images 3A and cross-sectional images 30A. The processing means 13 comprise at least a processor, data- and program-memory. The functional modules are implemented preferably as software modules which are stored in the program memory and are executed on the processor. One skilled in the art will understand that the functional modules can also be executed partially or completely through hardware.

The functional modules of the processing means 13 comprise a programmed positioning module which determines the position of a stored cross-sectional image 30A relative to the eye 3. The relative positioning takes place on the basis of the view images 3A, which are each assigned in each case to the cross-sectional images 30A. The determining of position of a cross-sectional image 30A takes place through position determination of the eye 3 relative to the ophthalmologic device 1. The relative position of the ophthalmologic device 1 to the eye 3 is thereby determined on the basis of the image of the illuminated cross-sectional portion 4A, of the natural features of the eye 3 and/or the depicted artificial reference features, for instance the depicted light markers 36. The position of a cross-sectional image 30A, or respectively the assigned image of the illuminated cross-sectional portion 4A, can be defined with reference to the natural features of the eye 3 contained in the respective view image 3A.

The functional modules of the processing means 13 comprise moreover a programmed composition module which positions a plurality of captured and stored cross-sectional images 30A relative to one another. The composition module merges, with knowledge of the geometric configuration of the ophthalmologic device 1, the captured and stored cross-sectional images 30A, in accordance with their relative position to the eye 3 or respectively to one another, into a three-dimensional image of the anterior chamber structures of the eye 3, in particular of the cornea 30.

The operational control and sequential control of the ophthalmologic device 1 can take place through the processing means 13 and/or through further electronic control modules (not shown).

The electrical supply of the ophthalmologic device 1 takes place through an internal energy source or through an external energy source connected by means of cable.

The embodiments of the ophthalmologic device 1 shown in FIGS. 1a, 2a, 4, 5, 6, 7 and 9 comprise a display 14 on which determined measurement values and/or application aids are shown.

The embodiments of the ophthalmologic device 1 shown in FIGS. 1a, 2a, 4, 5, 6, 7 and 9 comprise drive means 15 to rotate the light projector 11 and the image-capturing means substantially about a normal to the surface of the eye 3 turned toward the light projector 11 or to shift these components substantially perpendicular to this normal. As shown schematically in FIG. 9, the light projector 11 and the image capturing means 120, 121A, 121B, 121C, 122A, 122B, 122C are mounted for this purpose on a movable carrier device 10, which is driven by the drive means 15. The additional light source(s) 16 can be mounted on the carrier device 10 and co-moved, or can be mounted on the ophthalmologic device 1 in such a way that they are not coupled to the drive means 15. The drive means 15 preferably comprise a rotation driver, for instance an electromotor, which rotates the carrier device 10 about the optic axis Z of the eye. By means of rotation of the light projector 11 and of the image capturing means 120, 121A, 121B, 121C, 122A, 122B, 122C about the optic axis Z, the whole eye, in particular the entire cornea 30, is measured. In this configuration the most minimal measurement inaccuracies can be achieved owing to the high symmetry.

Figure 1B:
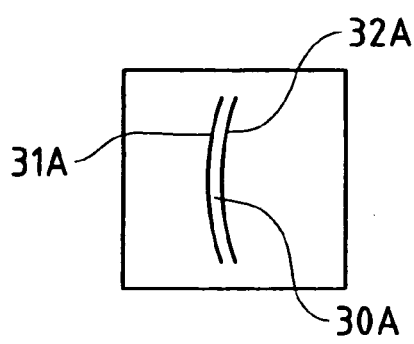
FIG. 1b shows a cross-sectional image of an illuminated cross-sectional portion of an eye (cornea).
Figure 1C:
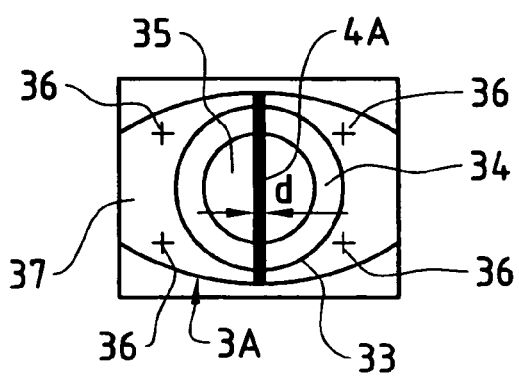
FIG. 1c shows a view image of an eye with an illuminated cross-sectional portion.
Figures 3, 4, 5:
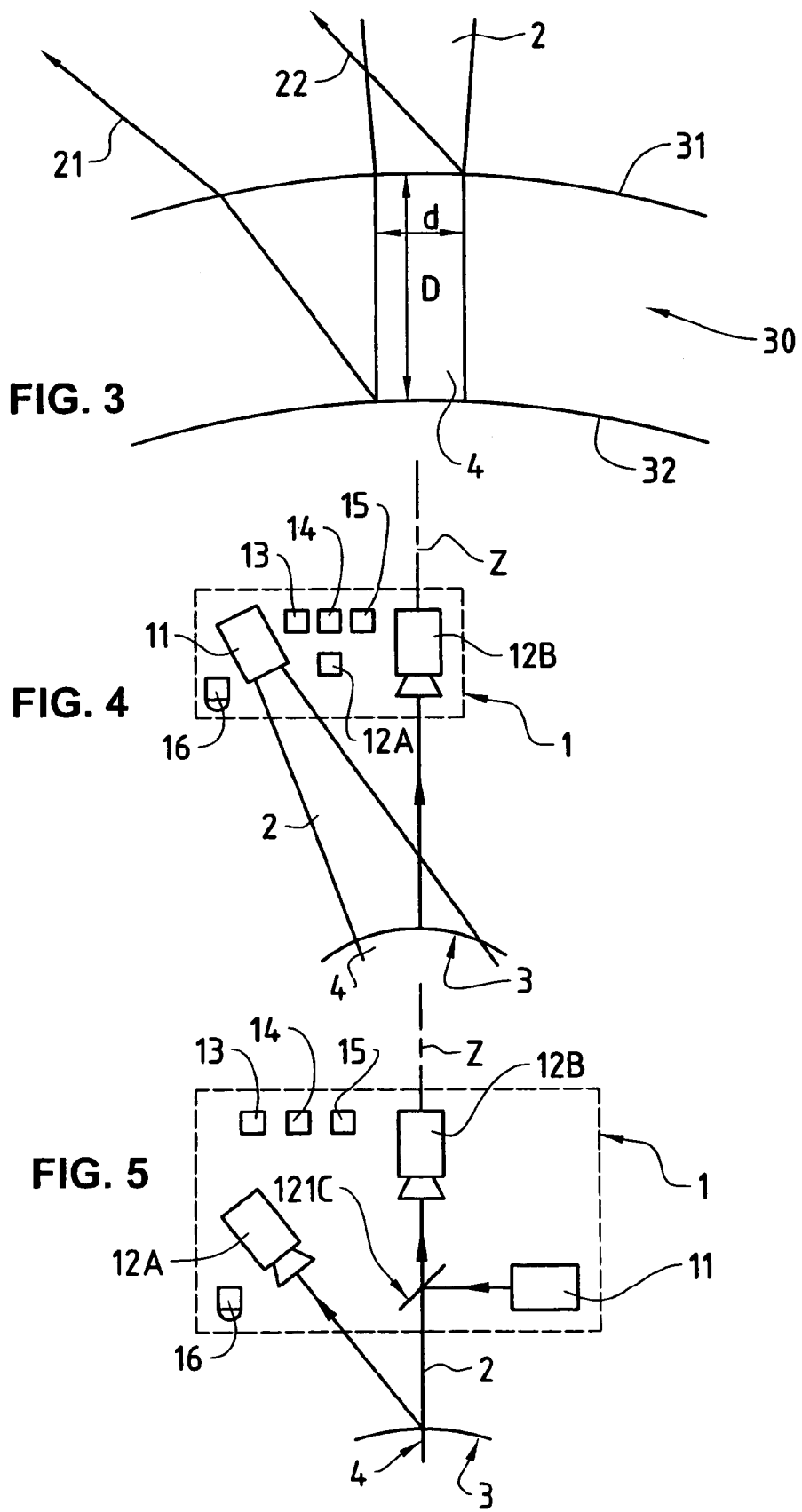
FIG. 3 shows a sectional view of an illuminated cross-sectional portion of an eye in which the ray trajectory of the incident and reflected beam of rays is illustrated schematically.
FIG. 4 shows a block diagram illustrating schematically a side view of an ophthalmologic device with a light projector and an image-capturing device, aligned along the optic axis of the eye, for capturing a view image of an eye.
FIG. 5 shows a block diagram illustrating schematically an ophthalmologic device with a light projector and an image-capturing device for capturing a view image of an eye in which the optic axis of the image-capturing device coincides with the beam of rays running through the cross-sectional portion.

As shown in FIG. 1a, the image capturing device 12A comprises for capturing and storing cross-sectional images 30A imaging optical elements 122A and an image converter 120, which are disposed in Scheimpflug configuration to the projected beam of rays 2. Shown in FIG. 1b is a cross-sectional image 30A, captured by the image capturing means 12A, of the illuminated cross-sectional portion 4 of the eye 3. For the sake of simplicity, further structures of the eye 3, such as iris or lens, are not shown in FIG. 1b. Visible in the cross-sectional image 30A are in particular a cross-sectional image of the anterior corneal surface 31A and a cross-sectional image of the posterior corneal surface 32A. In the embodiment according to FIG. 1a, the optic axis of the separate image capturing device 12B for capturing the view image 3A of the eye 3 is located outside the beam of rays 2. The view image 3A of the eye 3 shown in FIG. 1c indeed corresponds to a view image captured as a top view by an image capturing device 12B, the image capturing device 12B being disposed such that its optic axis runs substantially parallel to the optic axis Z of the eye 3 or the line of vision of the eye 3, or coincides with the optic axis Z or the line of vision of the eye 3, which is shown in FIGS. 4 and 5, for example. Visible in the view image 3A are in particular an image of the illuminated cross-sectional portion 4A with the finite thickness d, the projected light markers 36 as well as limbus 33, iris 34 and pupil 35 of the eye 3. Light markers are, for instance, highlights of light-emitting diodes or projected points. Places of projection are, for example, sclera 37 or cornea 30. The captured cross-sectional image 30A and the captured view image 3A are supplied to the processing means 13 and are stored there, assigned to one another, in the data store. The light projector 11 and the image capturing means 12A, 12B are moved by the drive means 15 into further imaging positions, and further cross-sectional images 30A and view images 3A are captured and are stored assigned to one another in each case.

Figure 2A:
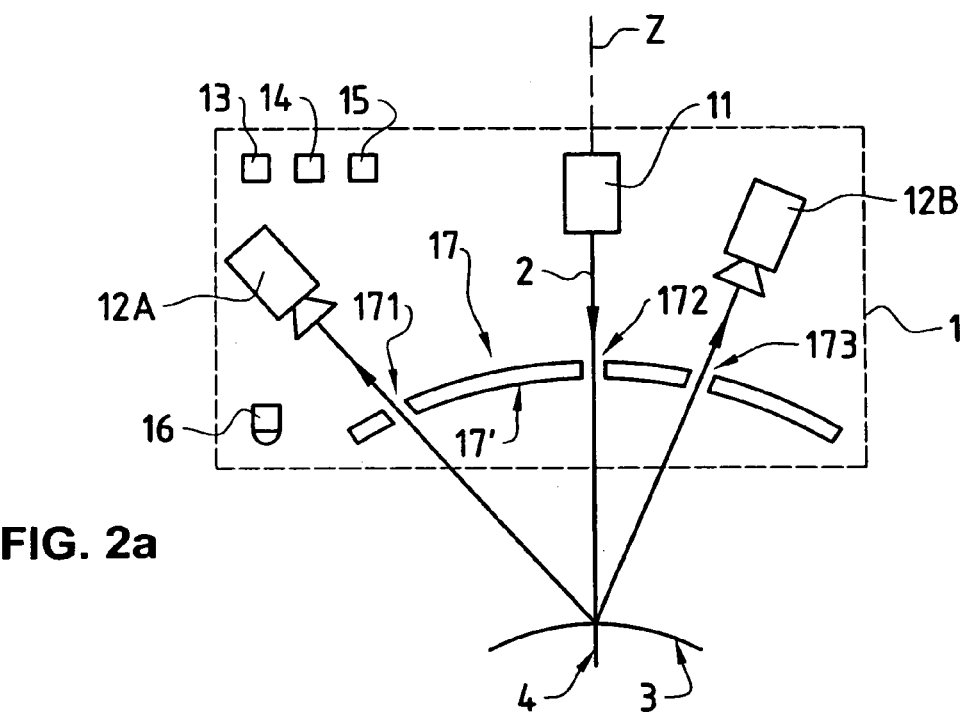
FIG. 2a shows a block diagram illustrating schematically an ophthalmologic device with a light projector, an image-capturing device for capturing a cross-sectional image of an eye, an image-capturing device for capturing a view image of the eye as well as a perforated screen element.
Figure 2B:
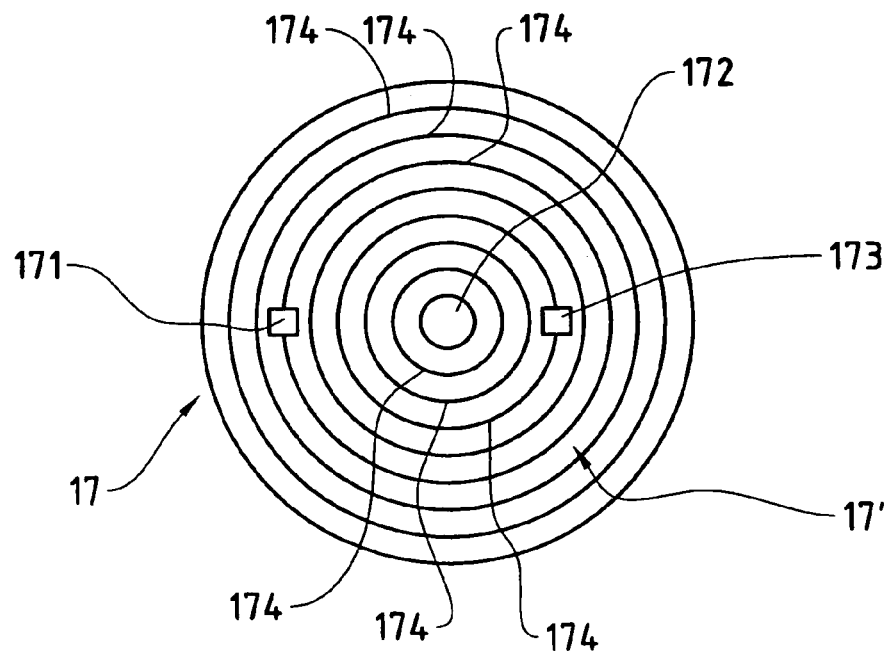
FIG. 2b shows a view of the side, turned toward the eye, of a screen element with openings and with a visible pattern.

Shown in FIG. 2a is an embodiment of the ophthalmologic device 1 comprising a perforated screen element 17. The openings 171, 172, 173 of the screen element 17 are each disposed such that the ray trajectories to the image capturing means 12A, 12B and to the light projector 11 can pass the screen element 17 unimpeded. Provided on the side of the screen element 17 turned toward the eye 3 is a visible pattern 17', a so-called placido pattern, for example with annuli 174, which is reflected by the surface of the eye 3, as is known from keratometers, for instance. Mounted on the screen element 17 can also be light sources turned toward the eye 3, for instance light projectors 16 for projection of light markers 36. Shown in FIG. 2b is a view of the side of the screen element 17, turned toward the eye 3, with openings 171, 172, 173 and with the visible pattern 17'. The reflection of the visible pattern 17' on the eye surface is pictured in the view image 3A by the image capturing device 12B, and can be used in the positioning of the cross-sectional images 30A as artificial reference pattern for determining the relative position of the ophthalmologic device 1 to the eye 3. The screen element 17 is preferably connected to the drive means 15 such that it is moved along with the light projector 11 and the image capturing means.

In an alternative embodiment, the screen element 17 can also be mounted on the ophthalmologic device 1 in such a way that it is not coupled to the drive means 15, the openings 171, 172, 173 being adapted accordingly. It should be mentioned here that the screen element 17 can also be disposed such that the image-capturing means 12A, 12B and/or the light projector 11 come to lie between the screen element 17 and the eye 3; the image capturing means 12A, 12B and/or the light projector 11 being thereby mounted, for example, on the side of the screen element 17 turned toward the eye 3.

FIG. 3 shows a sectional view of an illuminated cross-sectional portion 4 of the eye 3, in particular of the cornea 30. In FIG. 3, the reference numeral 31 designates the anterior corneal surface and the reference numeral 32 designates the posterior corneal surface. The cornea 30 is illuminated by the beam of rays 2 in the cross-sectional portion 4. As shown in FIG. 3, the beam of rays 2 has a finite thickness d. The reflected light rays 21, 22 allow the thickness D of the illuminated cross-sectional portion 4 in a cross-sectional image 30A to appear thicker than it actually is owing to the finite thickness d of the beam of rays. Since the geometric configuration of the light projector 11 and the image capturing means is known, the influence of the finite thickness d of the beam of rays 2 on the cross-sectional image 30A, or respectively on the measuring values determined from the cross-sectional image 30A, can be corrected with knowledge of the value of the finite thickness d. The finite thickness d of the beam of rays 2 can be determined particularly precisely when the view image 3A is captured in a view from above or top view by the image-capturing means.

In the embodiment of the ophthalmologic device 1 according to FIG. 4, the image-capturing device 12B is disposed such that a view image 3A is able to be captured corresponding to a top view of the eye 3. The optic axis of the image-capturing device 12B can be aligned in the application along the optic axis Z of the eye 3. As the side view in FIG. 4 shows, the beam of rays 2, which is shown in this view as a plane of light (or a light fan), is projected on the eye 3 in this embodiment laterally from outside the optic axis of the image-capturing device 12B.

Shown in FIG. 5 is a further embodiment of the ophthalmologic device 1 enabling a view image 3A as a top view of the eye 3. In the embodiment according to FIG. 5, the beam of rays 2 of the light projector 11, which runs through the cross-sectional portion 4, and the optic axis of the image-capturing device 12B for capturing the view image 3A coincide. This is achieved, for example, by the image-capturing device 12B and the light projector 11 being disposed such that their optic axes are situated in a common plane, the beam of rays 2 of the light projector 11 being directed on the optic axis of the image-capturing device 12B by means of the ray-redirecting optical elements 121C. Through the coincidence of the beam of rays 2, running through the cross-sectional portion 4, and the optic axis of the image-capturing device 12B, a particularly precise and simple determination of the finite thickness d of the beam of rays 2 is made possible as well as of the position of the cross-sectional images 30A from the view image 3A.

Figure 6:
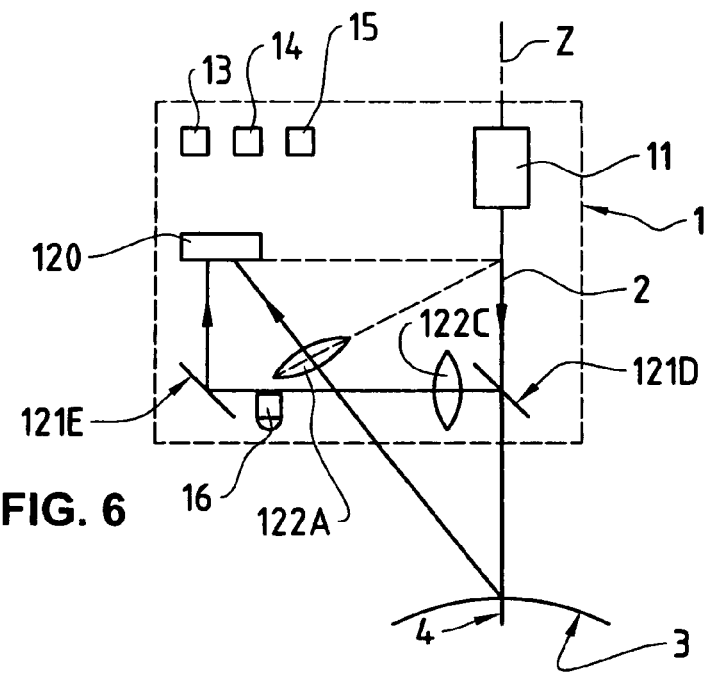
FIG. 6 shows a block diagram illustrating schematically an ophthalmologic device with a light projector and image-capturing means for capturing a cross-sectional image and a view image of an eye in which light rays for generating the view image and light rays for generating the cross-sectional image are supplied to a common image converter by means of ray-redirecting optical means.

Shown in FIG. 6 is a further embodiment of the ophthalmologic device 1 making possible a view image 3A with a top view of the eye 3 and in which the beam of rays 2, running through the cross-sectional portion 4, and the optic axis of the image-capturing means for capturing the view image 3A coincide. The embodiment according to FIG. 6 indeed has the advantage over that of FIG. 5 that both the cross-sectional image 30A and the view image 3A are captured by means of a single common image converter 120. The embodiment according to FIG. 6 is the result of a further development of the embodiment according to FIG. 1*a*, the light rays for generating the view image 3A out of the view from above being supplied to the image converter 120 by means of the ray-redirecting optical element 121D, which is disposed in the optical axis of the light projector 11, by means of the imaging optical elements 122C and by means of the ray-redirecting optical element 121E.

Figure 7:
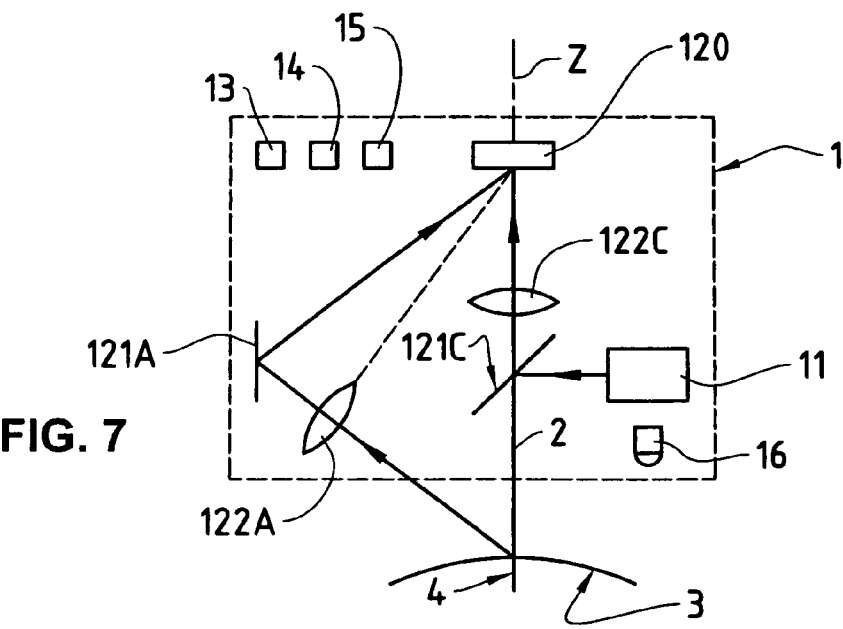
FIG. 7 shows a block diagram illustrating schematically a further embodiment of an ophthalmologic device with a light projector and image capturing means for capturing a cross-sectional image and a view image of an eye in which light rays for generating the view image and light rays for generating the cross-sectional image are supplied to a common image converter by means of ray-redirecting optical means.

Shown in FIG. 7 is a further embodiment of the ophthalmologic device 1 making possible a view image 3A with a top view of the eye 3 and in which the beam of rays 2, running through the cross-sectional portion 4, and the optic axis of the image-capturing means for capturing the view image 3A coincide. The embodiment according to FIG. 7 indeed has the advantage over that of FIG. 5 that both the cross-sectional image 30A as well as the view image 3A are captured by means of a single common image converter 120. Compared with the embodiment according to FIG. 6, it has in addition the advantage that it can be achieved in a simpler and more compact way. The embodiment according to FIG. 7 is the result of a further development of the embodiment according to FIG. 5; supplied to the image converter 120 being the light rays for generation of the cross-sectional image 30A by means of the imaging optical elements 122A, which, with the image converter 120, is disposed in Scheimpflug configuration with respect to the beam of rays 2 running through the cross-sectional portion 4, and by means of the ray-redirecting optical element 121A. The image capturing device 12B shown in FIG. 5 corresponds to the combination of the image converter 120 and the imaging optical elements 122C of FIG. 7.

Figure 8:
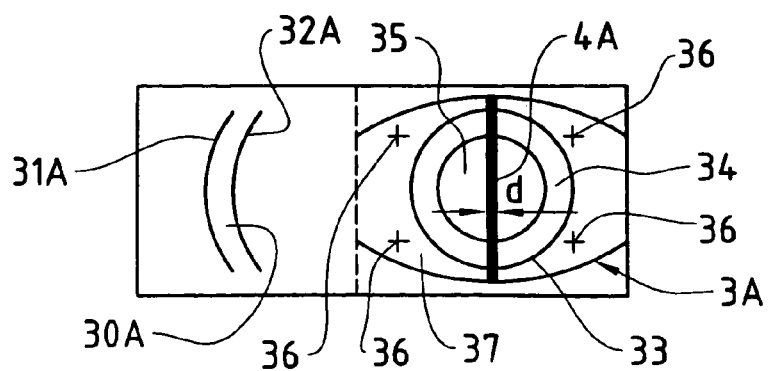
FIG. 8 shows a combined image with a cross-sectional image of an illuminated cross-sectional portion of an eye and a view image of the eye with the illuminated cross-sectional portion.

Shown in FIG. 8 is the combined cross-sectional image 30A and view image 3A, captured by the image converter 120 of the embodiments according to FIGS. 6 and 7. The combined image, as shown in FIG. 8, can be generated by the cross-sectional image 30A and the view image 3A being captured separately side-by-side. The cross-sectional image 30A and the view image 3A can also be captured partially or entirely superposed with the aid of color filters, known, for instance, from color cameras, and a plurality of light sources with different colors. An image separation is then carried out by the processing means 13 on the basis of the colors. It is also possible to use optical or electrical shutters and to capture the cross-sectional image 30A and the view image 3A quickly one after the other as separate images, so that relative movements between eye 3 and ophthalmologic device 1 have no appreciable influence. When using cameras, or respectively image converters, with frames and pulsed light sources, the cross-sectional image 30A and the view image 3A can be captured one after the other as two frames.

Figure 9:
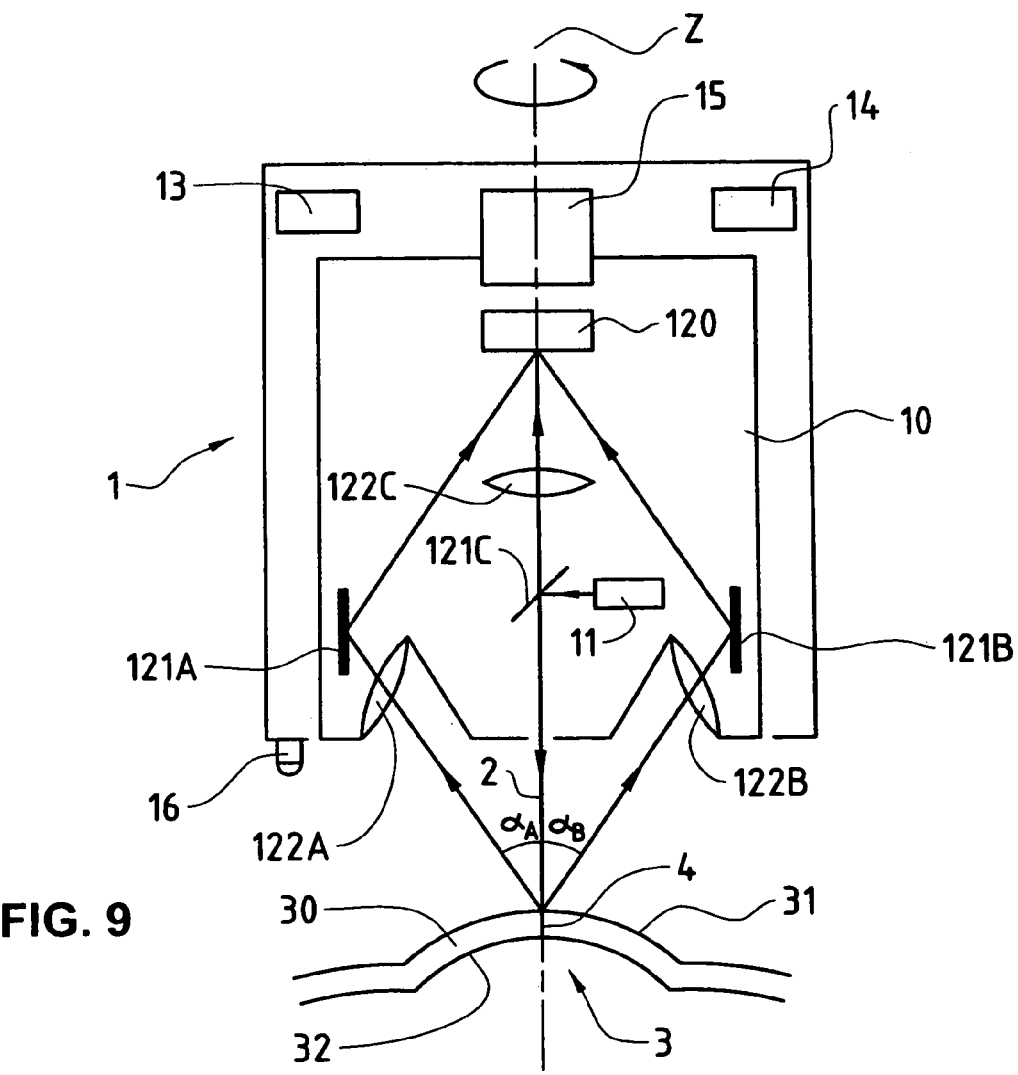
FIG. 9 shows a block diagram illustrating schematically an ophthalmologic device with a light projector and image capturing means for capturing two cross-sectional images and a view image of an eye in which light rays for generating the view image, and light rays for generating a first cross-sectional image from a first position, and light rays for generating a second cross-sectional image from a second position are supplied to a common image converter by means of ray-redirecting optical means.

Shown in FIG. 9 is a further embodiment of the ophthalmologic device 1 which makes possible a view image 3A with a top view of the eye 3 and in which the beam of rays 2, running through the cross-sectional portion 4, and the optic axis of the image capturing means for capturing the view image 3A coincide. The embodiment according to FIG. 9 is the result of a further development of the embodiment according to FIG. 7, the ophthalmologic device 1 being provided with further imaging optical elements 122B and with a further ray-redirecting optical element 121B to capture in addition a second cross-sectional image 30B. The imaging optical elements 122A and the ray-redirecting optical element 121A direct to the image converter 120 the light rays for capturing the cross-sectional image 30A from a first position at an angle of observation $\alpha_A$. The additional imaging optical elements 122B and the additional ray-redirecting optical element 121B likewise direct to the image converter 120 the light rays for capturing the cross-sectional image 30B from a second position at the angle of observation $\alpha_B$. The two positions are preferably located on different sides of the beam of rays 2, and the magnitudes of the observation angles $\alpha_A$ and $\alpha_B$ are preferably equal. Compared with the embodiment according to FIG. 7, the embodiment according to FIG. 9 has the advantage that measuring results which are determined from measuring values on the cross-sectional image 30A can be determined more precisely in the ophthalmologic device 1 according to FIG. 9 through averaging from two measuring values of two cross-sectional images 30A and 30B which have been captured from different positions. For example, the corneal thickness D can be determined more precisely from the measurement values $D_A$ and $D_B$, as described in the European patent application No. 02405272, unpublished at the time of filing of the present application.

Figure 10:
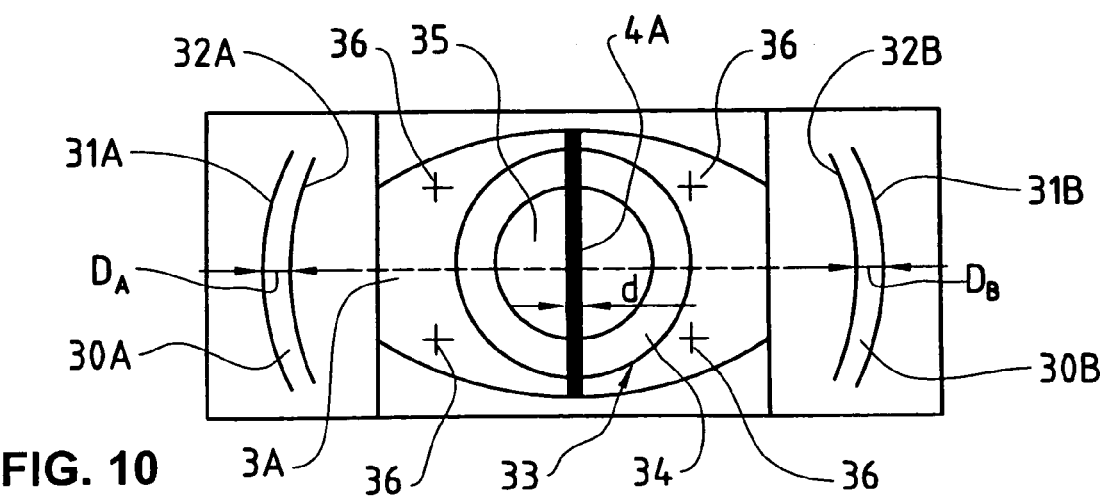
FIG. 10 shows a combined image with a first cross-sectional image of an illuminated cross-sectional portion of an eye from a first position, a view image of the eye with the illuminated cross-sectional portion, and a second cross-sectional image of the illuminated cross-sectional portion from a second position.

Shown in FIG. 10 is the combined cross-sectional image 30A, view image 3A and cross-sectional image 30B, captured by the image converter 120 of the embodiment according to FIG. 9. The combined image can be generated, as shown in FIG. 10, by the cross-sectional image 30A, the view image 3A and the cross-sectional image 30B being captured separately next to one another. The combined image can also be captured and shown differently, however, as already mentioned in connection with FIG. 8. Moreover one skilled in the art can carry out other image configurations, and, for instance, show the two cross-sectional images 30A, 30B directly next to each other above the view image 3A.

The functional modules of the processing means 13 also comprise furthermore programmed evaluation modules, for example measuring modules, which determine eye structures in the captured and stored cross-sectional images 30A, 30B, in particular images of the cornea with the anterior corneal surface 31A, 31B and the posterior corneal surface 32A, 32B, and determine distances, or respectively thicknesses, based thereon, in particular the measurement values $D_A$ and $D_B$ of the distances between the anterior corneal surface 31A, 31B and the posterior corneal surface 32A, 32B for determination of the corneal thickness D.

Finally it should be noted that the ophthalmologic device 1 is preferably executed as a compact measuring probe, it being possible for additional processing means for comprehensive capturing of the entire eye 3 to be implemented in an external processing unit, for instance in a personal computer, the exchange of data taking place via a communication link with contacts or a contactless communication link. Determined measurement results, for instance the local corneal thickness D or corneal topography, can be displayed on the display 14 or on a display of an external processing unit.

The invention claimed is:

1. An ophthalmologic device, comprising:
 a first light projector for projection of a beam of rays through a cross-sectional portion of an eye, in particular through a cross-sectional portion of the cornea of the eye,
 first image-capturing means for capturing and storing a cross-sectional image of at least one sub-area of the cross-sectional portion, illuminated by the first light projector, from a first position outside the beam of rays, which means are disposed in Scheimpflug configuration with respect to the beam of rays, and
 second image-capturing means for capturing a view image of the eye and for storing the captured view image assigned to the captured cross-sectional image, wherein
 the second image-capturing means are set up to capture and store the view image in such a way that the view image comprises an image of the cross-sectional portion illuminated by the first light projector, and
 the device comprises processing means for positioning the stored cross-sectional image relative to the eye on the basis of the stored assigned view image.

2. The device according to claim 1, wherein the processing means are designed to position the stored cross-sectional image relative to the previously stored cross-sectional images of the eye on the basis of the stored assigned view image.

3. The device according to claim 1, wherein the processing means are set up to determine the thickness of the cross-sectional portion, illuminated by the first light projector, of the eye on the basis of the stored view image.

4. The device according to claim 1, wherein the second image-capturing means and the first light projector are disposed such that the optic axis of the second image-capturing means coincides with the beam of rays running through the cross-sectional portion.

5. The device according to claim 1, wherein the first and the second image-capturing means are disposed such that their optic axes are situated in a common plane.

6. The device according to claim 1, wherein the first and the second image-capturing means comprise a common image converter, and the first image-capturing means comprise ray-redirecting optical elements, the ray-redirecting optical elements being disposed such that, for generation of the cross-sectional image, light beams are redirected to the common image converter.

7. The device according to claim 1, wherein the first and second image-capturing means comprise a common image converter, and the second image-capturing means comprise ray-redirecting optical elements, the ray-redirecting optical elements being disposed such that light beams are redirected to the common image converter for generation of the view image.

8. The device according to claim 1, wherein the first image-capturing means are set up to capture and store a second cross-sectional image of the sub-area of the cross-sectional portion illuminated by the first light projector, from a second position outside the beam of rays simultaneously with the capturing of the first cross-sectional image, the first position and the second position lying on different sides of a plane situated in the beam of rays.

9. The device according to claim 8, wherein the first image-capturing means comprise an image converter, and the first image-capturing means comprise ray-redirecting optical elements, the first of the ray-redirecting optical elements being disposed at the first position in such a way that light beams are redirected to the image converter for generation of a first cross-sectional image, and second of the ray-redirecting optical elements being disposed at the second position in such a way that light beams are redirected to the image converter for generation of the second cross-sectional image.

10. The device according to claim 1, wherein it comprises one or more additional second light projectors for projection of light markers on the eye, and the second image-capturing means are synchronized with the first light projector and with the second light projectors in such a way that, during the capturing and storing of the view image of the eye, the image of the cross-sectional portion illuminated by the first light projector and an image of the light markers projected by the second light projectors are co-captured and co-stored.

11. The device according to claim 1, wherein it comprises a screen element with a visible pattern, which screen element is disposed such that the visible pattern is situated on a side of the screen element turned toward the eye during application of the device, and the screen element being disposed such that the beam of rays is able to be projected unimpeded through the cross-sectional portion of the eye, and such that the cross-sectional image and the view image are able to be captured unimpeded by the first, respectively second, image-capturing means.

12. The device according to claim 1, wherein it comprises drive means to rotate the first light projector and the first and the second image-capturing means substantially about a normal to the surface of the eye turned toward the first light projector or to shift them substantially perpendicular to this normal.

13. The device according to claim 1, wherein the first light projector is designed such that it projects the beam of rays in the form of a light slit.

14. An ophthalmologic measuring method, comprising:
projecting a beam of rays through a cross-sectional portion of an eye, in particular through a cross-sectional portion of the cornea of the eye, by means of a first light projector,
capturing and recording a cross-sectional image of at least one sub-area of the cross-sectional portion, illuminated by the first light projector, from a first position outside the beam of rays, by means of first image-capturing means which are disposed in Scheimpflug configuration with respect to the beam of rays, and
capturing a view image of the eye and storing the captured view image assigned to the captured cross-sectional image, by means of second image-capturing means,
characterized by
capturing and storing of the view image in such a way that the view image comprises an image of the cross-sectional portion illuminated by the first light projector, and
determining the position of the stored cross-sectional image relative to the eye on the basis of the stored assigned view image.

15. The method according to claim 14, wherein the stored cross-sectional image is positioned relative to the previously stored cross-sectional images of the eye on the basis of the stored assigned view image.

16. The method according to claim 14, wherein the thickness of the cross-sectional portion of the eye illuminated by the first light projector is determined on the basis of the stored view image.

17. The method according to claim 14, wherein the second image-capturing means and the first light projector are disposed such that the optic axis of the second image-capturing means coincides with the beam of rays running through the cross-sectional portion.

18. The method according to claim 14, wherein the first image-capturing means and the second image-capturing means are disposed such that their optic axes lie in a common plane.

19. The method according to claim 14, wherein the first image-capturing means are provided with ray-redirecting optical elements, the ray-redirecting optical elements being disposed such that for generation of the cross-sectional image light beams are redirected to an image converter used jointly with the second image-capturing means.

20. The method according to claim 14, wherein the second image-capturing means are provided with ray-redirecting optical elements, the ray-redirecting optical elements being disposed such that for generation of the view image light beams are redirected to an image converter used jointly with the first image-capturing means.

21. The method according to claim 14, wherein simultaneously with the capturing of the first cross-sectional image a second cross-sectional image is captured of the sub-area of the cross-sectional portion, illuminated by the first light projector, by means of the first image-capturing means from a second position outside the beam of rays and is stored, the first position and the second position being established on different sides of a plane situated in the beam of rays.

22. The method according to claim 21, wherein first ray-redirecting optical elements of the first image-capturing means are disposed at the first position in such a way that for generating the first cross-sectional image they redirect light beams to an image converter of the first image-capturing means, and second ray-redirecting optical elements of the first image-capturing means are disposed at the second position in such a way that for generating the second cross-sectional image they redirect light beams to the image converter of the first image-capturing means.

23. The method according to claim 14, wherein light markers are projected on the eye by means of one or more additional second light projectors, and the second image-capturing means are synchronized with the first light projector and with the second light projectors in such a way that during the capturing and storing of the view image of the eye, the image of the cross-sectional portion illuminated by the first light projector and an image of the light markers projected by the second light projectors are co-captured and co-stored.

24. The method according to claim 14, wherein a screen element provided with a visible pattern is disposed such that the visible pattern is turned toward the eye, and the beam of rays is projected unimpeded through the cross-sectional portion of the eye, and the cross-sectional image and the view image are captured by the first, respectively second, image-capturing means in an unimpeded way.

25. The method according to claim 14, wherein the first light projector and the first and the second image-capturing means are rotated substantially about a normal to the surface of the eye turned toward the first light projector or are shifted substantially perpendicular to this normal.

26. The method according to claim 14, wherein the first light projector projects the beam of rays in the form of a light slit.

27. The method according to claim 14, wherein the second image-capturing means are disposed such that their optic axis coincides with the optic axis of the eye or runs substantially parallel to the optic axis of the eye.

28. The method according to claim 14, wherein the second image-capturing means are disposed such that their optic axis coincides with the line of vision of the eye or runs substantially parallel to the line of vision of the eye.

* * * * *